United States Patent [19]

Suzuki

[11] Patent Number: 5,349,955
[45] Date of Patent: Sep. 27, 1994

[54] TONOMETER

[75] Inventor: Takayoshi Suzuki, Chofu, Japan

[73] Assignee: Kowa Company Ltd., Japan

[21] Appl. No.: 88,182

[22] Filed: Jul. 6, 1993

[30] Foreign Application Priority Data

Jul. 27, 1992 [JP] Japan ................................. 4-198887
Sep. 29, 1992 [JP] Japan ................................. 4-258747

[51] Int. Cl.$^5$ .............................................. A61B 3/16
[52] U.S. Cl. ................................................... 128/645
[58] Field of Search ................................. 128/645-652

[56] References Cited

U.S. PATENT DOCUMENTS 4,621,644 11/1986 Eilers ................................... 128/652
5,174,292 12/1992 Kursar ................................. 128/645

FOREIGN PATENT DOCUMENTS 3718689 12/1988 Fed. Rep. of Germany ...... 128/645
 133171 of 1960 U.S.S.R. ............................. 128/645
1699416 12/1991 U.S.S.R. ............................. 128/645

Primary Examiner—Lee S. Cohen
Assistant Examiner—J. P. Lacyk
Attorney, Agent, or Firm—Bruce L. Adams; Van C. Wilks

[57] ABSTRACT

A tonometer is adapted to measure intraocular pressure by applying pressure onto of an eye being examined via its eyelid. The tonometer is provided with a pressure means that presses against the eyelid of a subject eye to thereby apply pressure to the eye. The load applied to the pressure means is detected by a Load sensor and used to calculate intraocular pressure of the eye. The tonometer with this arrangement is structurally simple and compact, operationally safe, and does not cause the patient to feel fear and discomfort.

5 Claims, 4 Drawing Sheets

TONOMETER

BACKGROUND OF THE INVENTION

1. Field of the Invention

The present invention relates to a tonometer for measuring intraocular pressure, and more particularly to a load-sensing type tonometer which measures intraocular pressure by applying pressure onto an eye being examined via its eyelid, and detecting the load being applied.

2. Description of the Prior Art

There are contact type and non-contact type conventional intraocular pressure measurement systems. In a contact type system a measuring member is pressed directly against the eyeball, and the pressure required to produce a given degree of deformation is used to establish the intraocular pressure. In the non-contact type system a stream of air is blown onto the surface of the cornea and the corneal deformation thus produced is measured, usually by an optical technique.

Contact type systems today offer a high degree of reliability. However, requiring as they do that part of the system apparatus be brought into direct contact with the cornea, a problem with contact type systems is that unless the operator is skilled in its operation, there is a risk that the cornea may be damaged.

While with the non-contact type system there is less risk of damaging the cornea, blowing a stream of air onto the cornea causes the patient to feel fear and discomfort. Thus, while it is called a non-contract method, this only means that there is no direct mechanical contact with the cornea. However, inasmuch as the measurement procedure involves subjecting the cornea to the direct application of force, it is no different from the contact type described above.

SUMMARY OF THE INVENTION

An object of the present invention is, therefore, to provide a tonometer that is simple and economical to make, easy to operate safely and does not cause feelings of fear and discomfort in the person whose eye is being examined.

According to the invention, a tonometer for measuring intraocular pressure by applying pressure onto an eye being examined via its eyelid and detecting a load being applied, comprises a pressure means that presses against the eyelid of a subject eye to thereby apply pressure to the eye, a drive means that generates the pressure applied by the pressure means, a load sensor that detects a load applied to the pressure means, and calculating means that calculates intraocular pressure of the eye based on the load detected by the load sensor when the pressure means presses on the subject eye.

With this arrangement, the intraocular pressure of the subject eye can be established from the relationship between detected load and the amount of eyeball displacement produced by the pressure exerted against the eyelid by the pressure member.

More specifically, the driving force of the drive means pushes a pressure rod against the eyelid and the load thus applied to the pressure rod at that point is detected by the load sensor and used as a basis for the calculating means to establish the intraocular pressure.

In accordance with the invention, the eye can be examined with the eyelid closed. This makes it possible to carry out the examination with absolutely no contact with the cornea of the eye that is being examined, unlike the conventional arrangements. Pressure is exerted on the eyelid, and the apparatus is easy to operate and there is none of the risk of damage to the cornea that is inherent in the conventional contact type system. Moreover, this invention also differs from the conventional non-contact system in that it does not employ a jet of air directed onto the cornea, and therefore does not inflict the type of discomfort and fear aroused by the conventional non-contact procedure.

In a preferred embodiment, the drive means is a resilient member. A tonometer preferably further comprises a cylinder that immobilizes the subject eye in a longitudinal direction by pressing against the peripheral portion of the eye via the eyelid thereof. In a preferred embodiment of the tonometer according to the invention, there is provided an eye fixation lamp that is used to fix the vision of the other eye to the front when intraocular pressure is being measured.

The calculating means corrects an intraocular pressure value to eliminate the effects of positional variation by the subject eye relative to the pressure rod occurring during measurement of intraocular pressure, the body temperature of the patient, the measurement environment and other such factors affecting intraocular pressure measurement.

In a preferred embodiment according to the invention, the pressure is exerted by moving the pressure means at a constant velocity, at which time the calculating means measures the intraocular pressure on the basis of changes over time in the load as detected by the load sensor.

Further features of the invention, its nature and various advantages will be more apparent from the accompanying drawings and following detailed description of the invention.

DETAILED DESCRIPTION OF THE PREFERRED EMBODIMENTS

Figure 1:
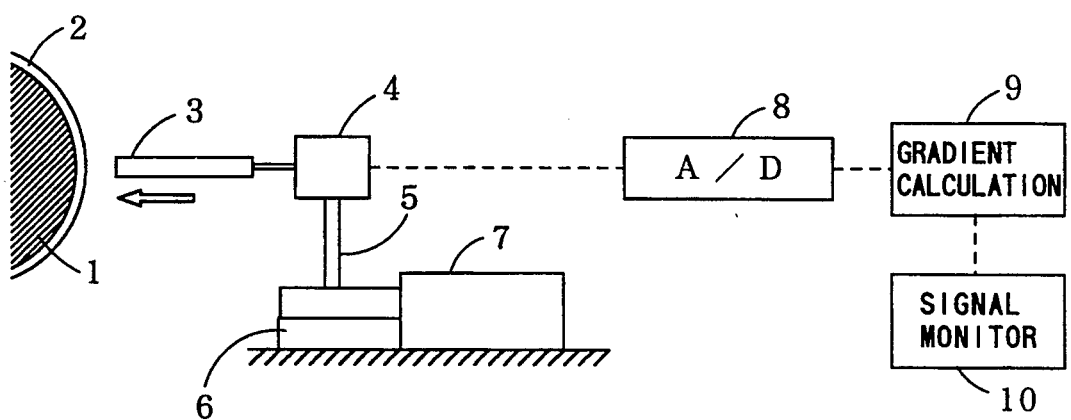
FIG. 1 is a block diagram showing the arrangement of the tonometer according to the present invention.

FIG. 1 shows the arrangement of a tonometer according to the present invention. In FIG. 1, reference numeral 1 denotes an eyeball of an eye being examined; in this embodiment the examination is conducted with an eyelid 2 closed. To perform the measurement, a pressure member 3 is moved at a constant velocity to press against the eyelid 2 over the eyeball 1, and the changing load is measured by a load sensor 4 rigidly affixed to the pressure member 3. The load sensor 4 is constituted by a prescribed type of strain gauge.

The load sensor 4 is attached, via a support 5, To a slide bed 6 that generates a pressing force towards the left (with respect to the drawing). The slide bed 6 is driven by a motor 7, but the movement of the slide bed 6 is controlled by a closed-loop system that moves the tip of the pressure member 3 towards the subject eye at a constant velocity. With this closed-loop constant velocity control system, the torque generated by the motor 7 will vary depending on the intraocular pressure, so the intraocular pressure can be obtained from changes in the load as detected by the load sensor 4.

Figure 2:
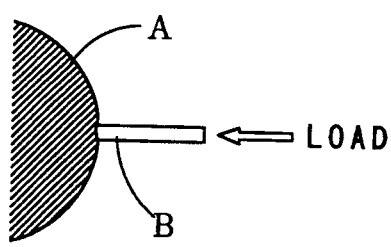
FIG. 2 is a diagram that illustrates the operating principle of the tonometer of this invention.
Figure 3:
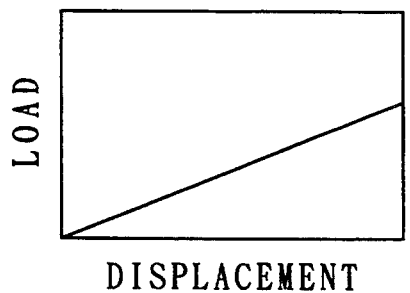
FIG. 3 is a graph that illustrates the operating principle of the tonometer of this invention.

FIG. 2 illustrates the principle of the present invention. Pressing a pressure member B against a resilient object A will give rise to relative changes in the load on the pressure member B and the degree of pressure member depression shown by FIG. 3. Here, the load is equal to the resilient force acting against the pressure, that is, to the intraocular pressure. Thus, intraocular pressure is defined as the load at a given degree of deflection (displacement).

Figure 4:
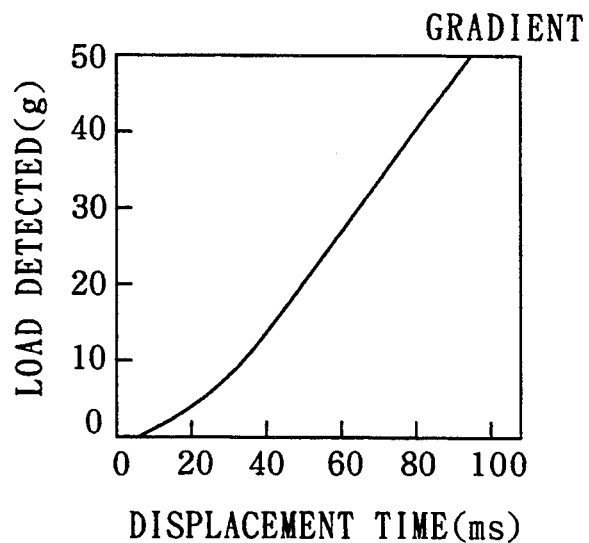
FIG. 4 is a graph relating to an example of a measurement made with the apparatus shown in FIG. 1.

The output of the load sensor 4 is converted to digital form by an A/D converter 8 and input to a gradient computation circuit 9 such as a personal computer, for example. The gradient computation circuit 9 obtains time-based changes (derivative) in load, as detected by the load sensor 4, and calculates the gradient (differential) thereof in terms of intraocular pressure, as shown by FIG. 4. The intraocular pressure measurements thus obtained are displayed on a CRT or other such display monitor 10.

In FIG. 4 the flattening of the curve from about zero to 20 ms is caused by the deformation of the eyelid 2. This type of change in load happens because the eyelid 2 usually has more give or resiliency than an eyeball with normal intraocular pressure. The eyelid 2 stops deforming about 20 ms after the commencement of pressure, after which changes in the load are a function of the intraocular pressure. This being the case, the intraocular pressure can therefore be measured by obtaining the gradient of the straight portion of the curve of FIG. 4. If there is something wrong with the eyeball that causes an elevation of the intraocular pressure, the gradient will be larger, while a lower intraocular pressure will produce a smaller gradient.

Strictly speaking, the straight-line gradient corresponds to the restoration constant of the eyeball. This restoration constant is highly dependent on the internal pressure, and the higher the internal pressure, the more the restoration force that is required. If the relationship between restoration constant and intraocular pressure is measured beforehand, the gradient computation circuit 9 can obtain the gradient of the straight-line portion of FIG. 4 as a restoration constant, thereby making it possible to obtain a measurement that is closer to the actual intraocular pressure.

In accordance with this embodiment, as the eye can be examined with the eyelid closed it is possible to carry out the examination with absolutely no contact with the cornea of the eye that is being examined, unlike the conventional arrangements. With pressure being exerted via the eyelid 2, the apparatus is easy to operate with none of the risk of damage to the cornea that is inherent in the conventional contact type system. This invention also differs from the conventional non-contact system in that it does not employ a jet of air directed onto the cornea, and therefore does not inflict the type of discomfort and fear aroused by the conventional non-contact procedure.

Furthermore, because the pressure member 3 is moved at a constant velocity, there is no need to use a displacement gauge, as the time values themselves can be regarded in that form as displacement values, it being sufficient to obtain differential of load with time. As such, this makes the apparatus simpler and cheaper to make.

The configuration described above relates to the basic implementation of the operating principle and if necessary may be modified in various ways. For example, in view of possible malfunction in the servo system of the motor 7, a stop may be provided to limit the amount by which the pressure member 3 can be advanced. In the embodiment described herein, the pressure member 3 is of a shape and material such as to preclude the pressure member 3 deforming during the measurement process. However, other materials may be used for the pressure member if the necessary variables are included in the computation circuitry. The pressure member may also be made to be replaceable, which would be more hygienic.

Figure 5:
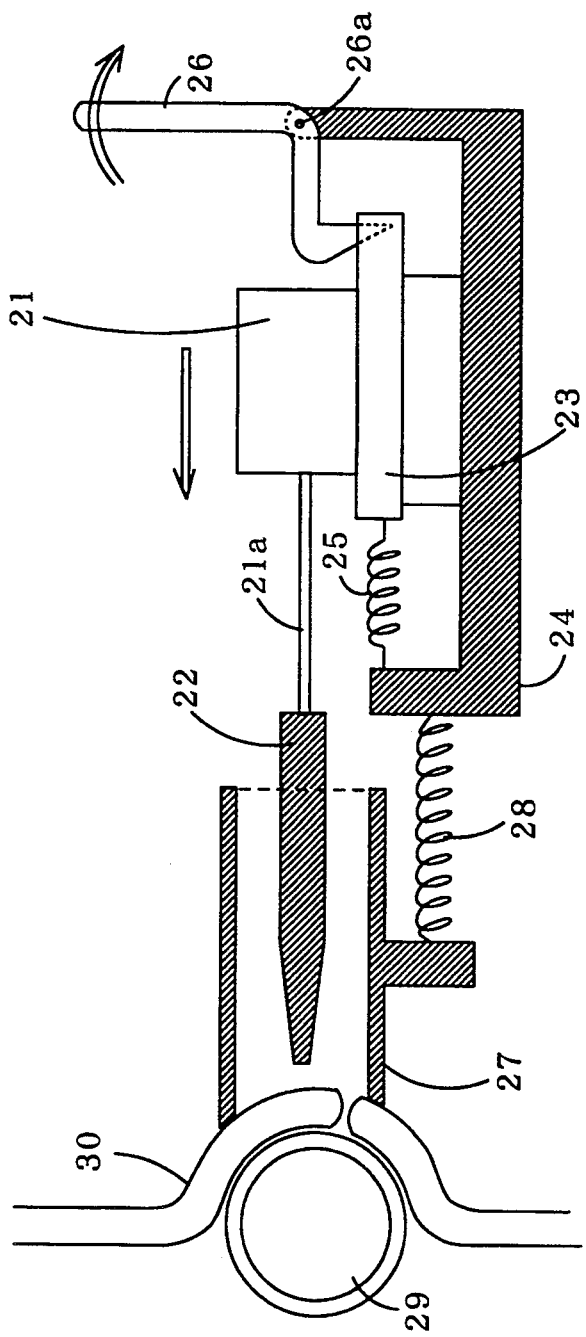
FIG. 5 is a side cross-sectional view of The arrangement of a load-sensing tonometer according to another embodiment of the present invention.

FIG. 5 shows another embodiment of the invention. In the tonometer of FIG. 5, a load sensor 21 is mounted on a slide bed 23 that is arranged on a surface plate 24 so that during measurement of intraocular pressure it can be slid forwards and backwards (to the left and right, with reference to the drawing sheet) along the optical axis of the eye being examined. The slide bed 23 is urged forwards by the force of a spring 25. Provided at the rear end of the surface plate 24 is a trigger 26 that is arranged so that it can pivot about a shaft 26a when operated by a person examining the eye. The lower edge of the trigger 26 is in disengagable engagement with the slide bed 23.

The load that is to be detected is applied to a shaft 21a that projects from the front of the load sensor 21. Affixed to the end of the shaft 21a is a pressure rod 22. This pressure rod 22 is for pressing against the eyelid 30 so as to thereby indirectly apply pressure to the eye 29. Arranged at the front of the surface plate 24 is a cylinder 27 that can be moved longitudinally backwards and forwards. The cylinder 27 is urged forwards by the force of a spring 28 and has a diameter that corresponds to the diameter of the eye 29. The pressure rod 22 is located inside the cylinder 27, where it is arranged along the central axis of the cylinder 27.

Figure 6:
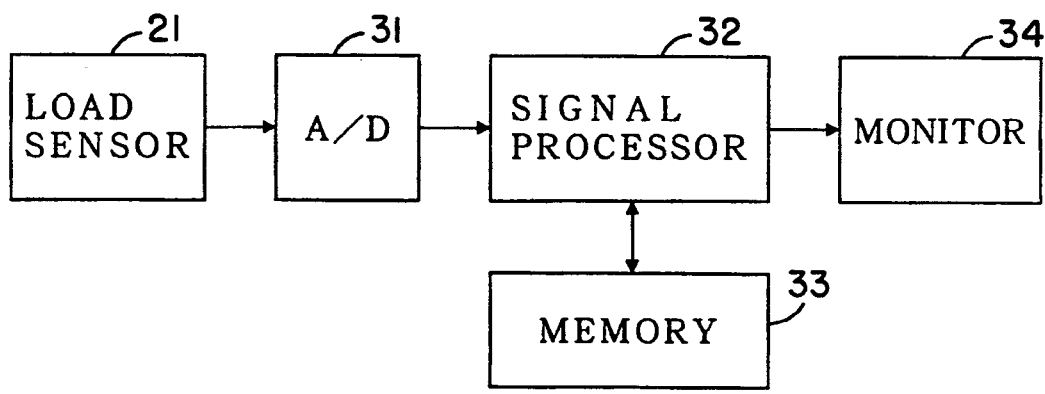
FIG. 6 is a schematic diagram showing the electrical circuit arrangement used in the tonometer whereby the intraocular pressure is obtained from the signal output of the load sensor.

FIG. 6 shows the electrical circuit arrangement used to obtain the intraocular pressure of the eye from the signals output by the load sensor 21. With reference to FIG. 6, the output of the load sensor 21 is subjected to analog-to-digital (A/D) conversion by an A/D converter 31. Reference numeral 32 denotes a signal processing circuit set, such as a microprocessor or the like, that processes load data signals output by the A/D converter 31 and calculates an intraocular pressure value, as described below. A memory 33 is used for storing load data, and a monitor 34 is used to display measured intraocular pressure values.

Figure 7:
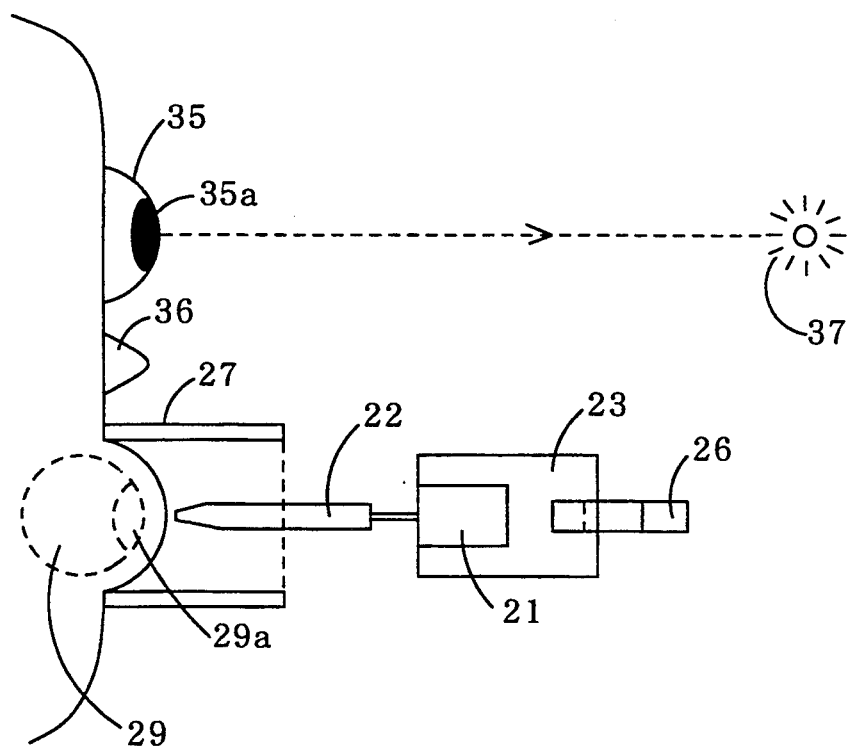
FIG. 7 is a drawing illustrating the arrangement during the intraocular pressure measurement process, as viewed looking down from above the patient's head.
Figure 8:
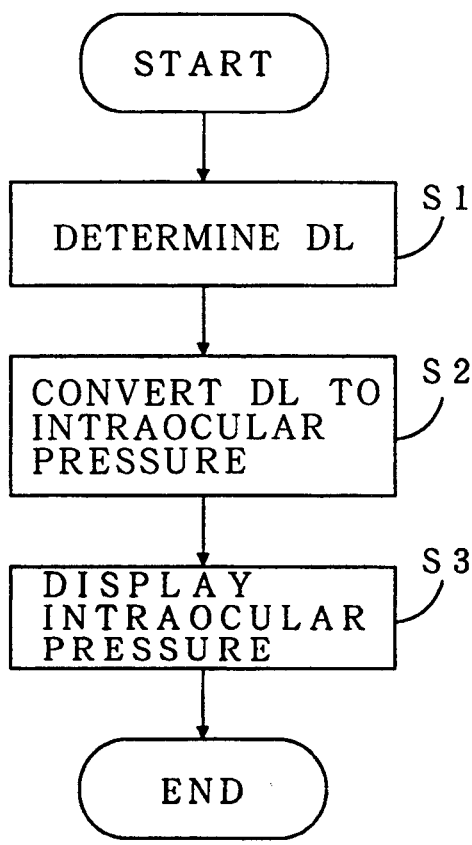
FIG. 8 is a flow chart of the signal processing circuit operation used to obtain the intraocular pressure.

The operation of the tonometer of this embodiment will now be explained with reference to FIGS. 7 to 10. FIG. 7 illustrates the arrangement during the intraocular pressure measurement process, as viewed from above. In FIG. 7, reference numeral 35 denotes the patient's other eye, i.e., the eye not undergoing examination, and 36 is the patient's nose. Also, in the tonometer according to this embodiment an eye fixation lamp 37 is provided to the rear of the load sensor 21. Prior to the execution of the measurement, the slide bed 23 is in the position shown in FIG. 5, engaged by the trigger 26.

As shown in FIG. 7, during the measurement process the patient is asked to keep eye 29 closed and the other eye 35 open. The cylinder 27 is brought into contact with the eyelid of eye 29 and arranged so that it is urged against the peripheral portion of the eyeball at a constant force provided by the spring 28, thereby immobilizing the eyeball in the longitudinal direction. The eye fixation lamp 37 is then switched on to fix the vision of the other eye 35. That is, with the vision of eye 35 fixed to the front, the position of the cornea 35a of the eye 35 is immobilized to the front. As the movement of both eyes is associated, this means that the position of the cornea 29a of eye 29 is also fixed towards the front, the direction along which the other eye 35 is fixed towards the eye fixation lamp 37, directly facing the pressure rod 22. When the trigger 26 is now pulled by the operator, the trigger 26 is disengaged from the slide bed 23 and the slide bed 23 is moved forward by the force of the spring 25, whereby the pressure rod 22 presses against the eyelid, thereby exerting pressure on the eyeball of the eye 29 under a load that is detected by the load sensor 21.

Figure 9:
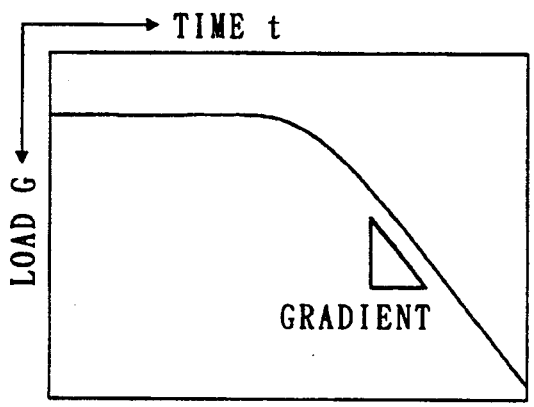
FIG. 9 is a graph showing the relationship between the load applied to the pressure rod during measurement of intraocular pressure, and time.
Figure 10:
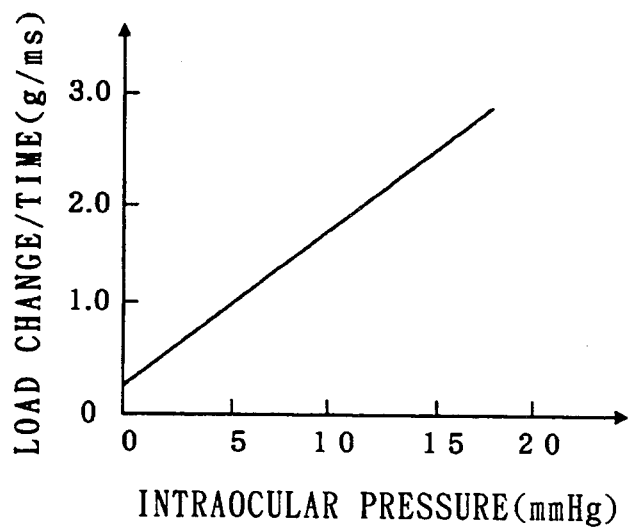
FIG. 10 is a graph showing the correlation between differential of load with time and intraocular pressure based on the results of experiments.

The signals output by the load sensor 21 are subjected to A/D conversion by the A/D converter 31 and are then input to the signal processing circuit 32 and written into the memory 33 as load data. This load data is then read out of memory 33 by the signal processing circuit 32, and, as shown in the flow chart of FIG. 8, the change in load relative to time (differential of load with time DL) is obtained (step S1), and the correlation between differential of load with time and intraocular pressure is used to convert the differential of load with time DL to an intraocular pressure value (step S2). Thus, while usually the hardness of the eyeball is measured from the relationship between load and the amount by which the pressure rod 22 is pressed in, in this invention the fact that the pressure rod 22 is moving is used to measure the hardness of the eyeball based on changes in the load relative to time. FIG. 9 shows this relationship between load and time. As the intraocular pressure is determined by the apparent hardness of the eyeball, the intraocular pressure can be calculated from the time-based rate of change in the load. That is, based on the results of comparative experiments using loading tonometry, as shown by FIG. 10, there is a directly proportional correlation between differential of load with time and intraocular pressure, and this correlation can be used to convert load change/time to intraocular pressure.

The intraocular pressure value thus obtained by the signal processing circuit 32 is then displayed on the monitor 34 (step S3).

The intraocular pressure value thus obtained is compensated by the signal processing circuit 32 to eliminate the effects of positional variation by the eye 29 relative to the pressure rod 22 occurring during the intraocular pressure measurement, the body temperature of the patient, the measurement environment and other such factors that can affect intraocular pressure measurements.

In the above-mentioned embodiment, using a spring to move the slide bed 23, and thereby the load sensor 21, greatly simplifies the structure and enables the overall size of the tonometer to be reduced. Also, using the cylinder 27 to fix the longitudinal position of the eyeball of the eye 29 prior to the application of pressure by the pressure rod 22 makes it possible to eliminate from the load amount detected by the load sensor 11, the component produced by overall eyeball motion, thereby increasing measurement accuracy. Using the eye fixation lamp 37 to fix the vision of the other eye 35 to thereby ensure that the cornea 29a of the eye 29 being examined faces to the front, although the eye is closed, also helps to improve the measurement accuracy.

It is understood, of course, that the pressure rod 22 can be moved at a constant velocity by employing a mechanism as used in the embodiment in FIG. 1 and the detected load can be processed by the gradient calculation circuit 9 to determine the intraocular pressure of the eye.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. A tonometer for measuring intraocular pressure by applying pressure onto an eye of a person being examined, comprising:

pressure means for pressing against an eyelid of an eye of a person being examined to thereby apply pressure to the eye;

drive means for driving the pressure means against the eye to cause the pressure means to apply pressure to the eye;

load sensor means for detecting a load applied to the pressure means;

calculating means for calculating intraocular pressure of the eye based on the load detected by the load sensor means when the pressure means presses on the eye; and means for immobilizing the eye during the application of pressure thereto by the pressure means.

2. A tonometer as set forth in claim 1, in which the drive means comprises a resilient member.

3. A tonometer as set forth in claim 1, wherein the means for immobilizing comprises a cylinder movable into contact with the eye to immobilize the eye in a longitudinal direction by pressing against the peripheral portion of the eye via the eyelid thereof.

4. A tonometric system for measuring intraocular pressure by applying pressure onto an eye of a person being examined, comprising:

pressure means for pressing against an eyelid of an eye of a person being examined to thereby apply pressure to the eye;

drive means for driving the pressure means against the eye to cause the pressure means to apply pressure to the eye;

load sensor means for detecting a load applied to the pressure means;

calculating means for calculating intraocular pressure of the eye based on the load detected by the load sensor means when the pressure means presses on the eye; and an eye fixation lamp adapted to be disposed to fix the vision of the person's other eye to the front when intraocular pressure is being measured.

5. A tonometer for measuring intraocular pressure by applying pressure onto an eye of a person being examined, comprising:

pressure means for pressing against an eyelid of an eye of a person being examined to thereby apply pressure to the eye;

drive means for driving the pressure means at a constant velocity against the eye to cause the pressure means to apply pressure to the eye;

load sensor means for detecting a load applied to the pressure means; and calculating means for calculating intraocular pressure of the eye on the basis of changes over time in the load as detected by the load sensor means.

* * * * *